United States Patent [19]
Kring

[11] 4,208,371
[45] Jun. 17, 1980

[54] GASEOUS CONTAMINANT DOSIMETER WITH DIFFUSION DEVICE THEREFOR AND METHOD

[75] Inventor: Elbert V. Kring, Wilmington, Del.

[73] Assignee: E. I. Du Pont de Nemours and Company, Wilmington, Del.

[21] Appl. No.: 922,546

[22] Filed: Jul. 7, 1978

[51] Int. Cl.² .................... B01D 53/22; B01D 59/10; G01N 31/22; G01N 33/00

[52] U.S. Cl. ................................. 422/61; 23/232 R; 55/158; 73/23; 422/86

[58] Field of Search .................. 55/158; 428/398, 401; 264/261–263, 136, 137; 23/232 R; 422/59, 61, 86; 65/4 A, 4 B; 73/23, 27; 324/29

[56] References Cited

U.S. PATENT DOCUMENTS

| | | | |
|---|---|---|---|
| 2,752,731 | 7/1956 | Altosaar | 65/4 A |
| 2,996,419 | 8/1956 | Schmick | 65/4 A |
| 3,033,731 | 5/1962 | Cole | 264/263 X |
| 3,262,251 | 7/1966 | Hicks, Jr. | 55/158 |
| 3,279,902 | 10/1966 | Gardner | 65/4 A X |
| 3,311,454 | 3/1967 | Kemeny et al. | 422/86 |
| 3,372,082 | 3/1968 | Kometani et al. | 428/398 X |
| 3,476,515 | 11/1969 | Johnson et al. | 422/61 X |
| 3,754,882 | 8/1973 | Esdonk et al. | 65/4 B |
| 3,884,814 | 5/1975 | Vogt et al. | 55/158 X |
| 3,940,469 | 2/1975 | Steigelmann et al. | 428/348 X |
| 3,966,440 | 6/1976 | Roberts | 422/86 X |
| 4,108,764 | 8/1978 | Kaneko et al. | 55/158 X |

*Primary Examiner*—Michael S. Marcus

[57] ABSTRACT

A personal dosimeter for measuring the average concentration of a gaseous contaminant over a given period of time is provided. The dosimeter comprises a sealed pouch having a reaction chamber, which contains a gas-collecting medium, and at least one compartment. Each compartment can be separately sealed and can contain a different reagent, the seals being individually breakable such that the reagents can be separately released into the reaction chamber. Into the pouch is sealed a gas diffusion device which consists of a formation of parallel, potted, hollow fibers or filaments. The diffusion device is oriented such that one end of the fibers is open to the atmosphere and the other end communicates with the interior of the reaction chamber.

20 Claims, 4 Drawing Figures

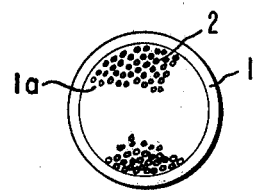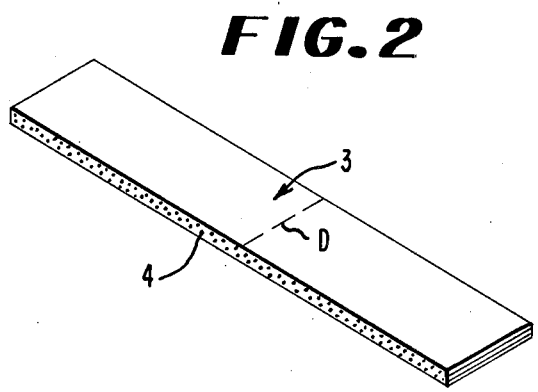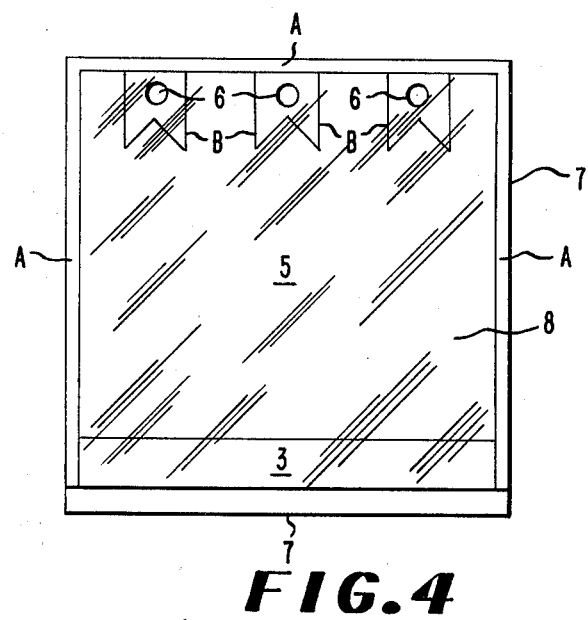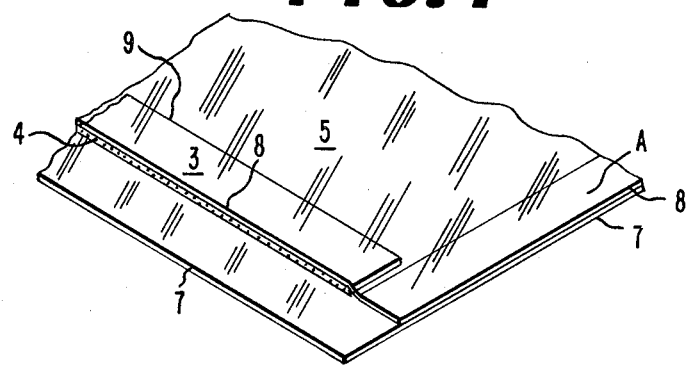

GASEOUS CONTAMINANT DOSIMETER WITH DIFFUSION DEVICE THEREFOR AND METHOD

BACKGROUND OF THE INVENTION

1. Field of the Invention

This invention is related to a personal dosimeter for registering gas contaminants in the atmosphere and to a gas diffusion device to be used therein. More particularly it is related to a self-contained dosimeter capable of integrating the exposure level of a gas contaminant over a given period of time.

2. Description of the Prior Art

In response to the increasing concern about the health of workers who are exposed to harmful pollutants in the air, it has become necessary to monitor the concentration of the air-borne contaminants. One development for this purpose involved a rather large air pump which would force air to be sampled through a filter, trapping particulate contaminants. This obviously is unavailing for the monitoring of gas contaminants and, even for particles, is not accurate to determine concentration of the particles in the sampled atmosphere.

Personal sampling devices which are worn by individual workers and which passively collect the contaminants have also been used. For example, a device which utilizes the molecular diffusion of the gas to be monitored to collect the sample has been described in American Industrial Hygiene Association Journal, Volume 34, pages 78–81 (1973). This device, however, requires that the collecting medium be removed therefrom, and carefully treated with reagents which must be exactly-measured at each analysis. The disassembly of the device and use of cumbersome reagents required for each analysis are disadvantageous.

Other personal sampling devices have used membranes which are selectively permeable to the gaseous contaminant to be monitored. Behind the membrane is usually sealed an absorbing medium for the gas. After exposure, a reading is taken of the contaminant concentration in the medium which is relatable mathematically to the contaminant's average concentration in the atmosphere over the time of exposure. However, at high concentrations, these membranes pass too much of the gas and the correlation between the concentration in the absorbing medium and that in the atmosphere is destroyed.

Therefore, there remains a need for a personal gas contaminant dosimeter for gaseous contaminants which accurately integrates, that is, indicates the average concentration of the gaseous contaminant over a given time period, and which easily lends itself to analysis without removal of the gas-collecting medium or bothersome addition of other elements.

SUMMARY OF THE INVENTION

According to the present invention, there is provided a gas diffusion device to restrict the flow of a gaseous contaminant which comprises:

A plurality of parallel, potted, hollow fibers, said fibers being substantially non-hygroscopic and inert to said gaseous contaminant and having an inside diameter of 15–1000 microns; and potting material which fills the longitudinal spaces between said fibers, wherein at least one of said fibers and said potting material is impermeable to said gaseous contaminant.

According to another aspect of the invention, there is provided a personal dosimeter for measuring the average concentration of a gaseous contaminant over a given period of time comprising: a sealed pouch-like receptacle of a pliable polymeric material, said receptacle having a reaction chamber adapted to contain a gas-collecting medium and at least one compartment separately sealed and adapted to contain a testing reagent, the seals of each compartment being individually breakable such that the reagents can be separately released into the reaction chamber; and a gas diffusion device which consists of a formation of parallel, potted, hollow fibers, the diffusion device being sealed into the receptacle and oriented such that one end of the fibers is open to the atmosphere and the other end communicates with the interior of the reaction chamber.

BRIEF DESCRIPTION OF THE DRAWINGS

FIG. 1 is a top view of a gas diffusion device in the form of a plug.

FIG. 2 is a magnified perspective view of another gas diffusion device within the present invention in the form of a ribbon.

FIG. 3 is a top view of a gaseous contaminant dosimeter utilizing the gas diffusion device of FIG. 2.

FIG. 4 is a partial perspective view, in magnification, of the dosimeter of FIG. 3.

DETAILED DESCRIPTION OF THE INVENTION

FIGS. 1 and 2 illustrate preferred embodiments of the gas diffusion device of the present invention having a plurality of hollow fibers or filaments closely packed together by a potting material which fills the longitudinal spaces between the fibers. The diffusion device is based on the molecular diffusion of gases through an elongated orifice, herein embodied by the channel in each hollow fiber. It is to be understood at the outset that the present invention is concerned only with the diffusion of the gas through the channels of the fibers rather than the permeation of the gas through the walls of the fibers.

The mathematical expression for the molecular diffusion, or transfer, of a gaseous contaminant in the air through an orifice is given by Fick's Law as shown in American Industrial Hygiene Association Journal, Volume 34, pages 78–81 (1973). When used to calculate the quantity of gaseous contaminant transported by molecular diffusion through the orifice over a given time, it is expressed as $Q = 3600 \cdot D \cdot A \cdot t \cdot (C - C_1) \cdot 1/Z$ where $Q$ = quantity of gaseous contaminant transferred (moles)

$D$ = diffusion coefficient of the gaseous contaminant through air (cm$^2$/sec)

$A$ = cross-sectional area of the orifice (cm$^2$)

$t$ = time of exposure (hours)

$C$ = concentration of the contaminant in the atmosphere (moles/cm$^3$)

$Z$ = distance in direction of diffusion, herein orifice length (cm)

$C_1$ = concentration of the contaminant (moles/cm$^3$) at the end of the orifice away from the atmosphere, that is, after diffusion through distance Z If the concentration at the end of the orifice away from the atmosphere is maintained at zero by a suitable absorbing or adsorbing medium, then $C_1$ drops out of the equation. The usual units of exposure to gaseous atmosphere-contaminants are parts contaminant per million parts air (ppm). For instance, one ppm at 21° C. and one atmosphere pressure is $0.0414 \cdot 10^{-9}$ moles/cm$^3$. With this substitution, Fick's Law becomes $$Q = 1.59 \cdot D \cdot A \cdot t \cdot (\text{ppm of gas contaminant}) \cdot 1/Z \cdot 10^{-7}.$$

Values of D for various gaseous contaminants are readily obtainable from the literature. Fick's Law applies to each hollow fiber in the diffusion device.

With respect to FIG. 1, there is shown a diffusion device in the form of a plug. Hollow fibers 2, the ends of some of which are shown, greatly enlarged, are potted in a potting material 1 which not only can form a rim around the formation of fibers 2, as shown, but also fills the longitudinal spaces 1a between fibers. The fibers 2, which are open-ended, are oriented perpendicularly to the plane of FIG. 1. Similarly, FIG. 2 shows a diffusion device in the form of a ribbon 3 in which the thickness of edge 4 shown greatly enlarged and the open-ended fibers, contained therein, the ends of some of which are shown in edge 4, extend the length of, and are oriented in the direction of, line D.

It is to be understood that, as further described below, the diffusion devices of FIGS. 1 and 2, and equivalent facsimiles, are composed for the most part of the hollow fibers. The potting material acts mainly to give shape and structural stability to the formation of closely-packed hollow fibers and to fill the longitudinal spaces between the fibers to aid in the prevention of permeation of the gaseous contaminant through the walls of the hollow fibers. For example, a diffusion device similar to the one shown in FIG. 1, having a fiber-formation diameter of 3.15 mm can contain over 6000 hollow fibers.

The hollow fibers can be made from any of the conventionally known polymeric materials so long as they are substantially non-hygroscopic and inert to both the gaseous contaminant to be measured and to the gas-collecting medium, which can be present if the diffusion device is used in an integrating personal dosimeter.

By inert, it is meant that the material from which the hollow fibers are constructed does not absorb, adsorb, or react with either the gaseous contaminant or gas-collecting medium. By non-hygroscopic, it is meant that the hollow-fibers do not interact with water or water vapor in a way which would substantially vary the hollow cross-sectional area of the fibers. The operation of the diffusion device is thus substantially insensitive to humidity fluctuations.

The hollow fibers can be made of, for example, polyesters, polyolefins, or acrylic. Preferred materials of construction are polypropylene, polyethylene, polyethylene terephthalate, and polymers or copolymers of tetrafluoroethylene and hexafluoropropylene. The hollow fibers can be prepared by any of the conventionally known methods such as by melt extrusion or melt spinning, which is preferred. With respect to melt spinning, the methods described in any of U.S. Pat. No. 2,999,296, No. 3,313,000, or No. 3,397,427, for example, produce hollow fibers of various inside and outside diameters suitable for use herein. It has been found that fibers having an inside diameter of 15–1000, preferably 15–500 microns effectively perform the integrating function of the present invention. When the gaseous contaminant is organic, inside diameters of 500 microns or greater are preferred. When the gaseous contaminant is inorganic, a preferred range of inside diameters is 15–45 microns with the most preferred being 25–40 microns. Although the cross-section of the channel through the hollow fibers is normally round, it is to be understood that is is not necessarily so. Therefore, as used herein, diameter refers to the longest straight dimension of such cross-section.

The potting material can be any molding compound or the like which is substantially firm at room temperature, approximately 21° C. The material should also be inert to the collecting medium and the fibers, and preferably to the gaseous contaminant as well. Many commonly known paraffin waxes are suitable for this purpose, as are conventional epoxy-based or other polymeric molding compounds.

One preferred epoxy-based molding compound comprises an epoxy resin of the epichlorohydrin-bisphenol-A type of epoxide equivalent weight 250–280 which is amine-curable. A suitable resin of this type is available, for example, as Epi-Rez ® 50821 available from Celanese Corporation.

Other preferred potting materials are ionomer resins such as the ionic copolymers of alpha-olefins and alpha, betaethylenically unsaturated carboxylic acids of 3–8 carbon atoms having 10–90% of the carboxylic acid groups neutralized with metal ions. Such materials are disclosed in U.S. Pat. No. 3,264,272 issued Aug. 2, 1966 to R. W. Rees.

To insure that the gaseous contaminant diffuses only through the channels of the hollow fibers, either the fibers or the potting material which fills the longitudinal spaces between the fibers must be impermeable to the gaseous contaminant.

Preparation of a diffusion device within the present invention can be achieved as follows:

A hollow fiber having the desired inside diameter is prepared by any of the aforementioned methods and the single, long strand of fiber thus formed is wound around a hanking wheel until the desired fiber quantity is attained. The hanked formation is then removed from the wheel, folded to "double" the number of fiber strands in the formation, and placed in intimate contact with the potting material into an elongate mold. The transverse cross section of the mold is substantially of the size and shape desired for the diffusion device. For example, the transverse cross section of the mold either would be circular to form the diffusion device of FIG. 1 or would be shaped similarly to edge 4 to form the device of FIG. 2.

As an illustration, a device of FIG. 2 of preferred dimensions can be formed by using a two-part mold having a transverse cross section measuring approximately 5.1 cm by 1.1 mm. A 2-mil thick film of an ionic copolymer as described above is placed in each half of the mold. The folded hank of parallel fibers, prepared as described above, is placed into the mold which is then forcibly closed, sandwiching the fibers between the two films. The mold is heated to 120° C. for 15–20 minutes during which time the films of the ionic copolymer potting material melt and wick into the longitudinal spaces between the fibers. Pressure is also applied to the mold to enhance the wicking and to squeeze out excess potting material.

The mold is allowed to cool and the strip of parallel, potted fibers thus formed is removed and can be cut transversely to give open-ended fibers of the desired length, oriented as is line D in FIG. 2.

A device according to FIG. 1 can be made by placing a hank of hollow fibers, as above, into a mold of circular transverse cross section. A liquid epoxy, for example, can be poured into the mold to saturate the fibers and then the epoxy can be cured, simultaneously applying pressure to the mold to squeeze out excess epoxy and to insure that the longitudinal spaces between fibers are substantially filled. After cure, the potted-fiber rod thus formed can be cut transversely to give a plug of potted, open-ended fibers as in FIG. 1.

Apart from the length of the hollow fiber, the size of the diffusion device need not be rigidly controlled and is normally dependent only on the anticipated enduse of the device. The fiber length, while also not critical, does however effect the operation of the device. As can be seen from Fick's law, the quantity of gas transferred by diffusion through the fiber is inversely proportional to the length of the fiber. It has been found that when the device is used, for example, in a gaseous contaminant dosimeter, fibers having an inside diameter of 15–1000 microns can have a length of 2.0–8.0 mm and preferably 3.0–6.5 mm. These measurements provide optimum performance of the integrating function of a dosimeter using the diffusion device.

It has further been found that the number of hollow fibers in the diffusion device is also not critical and theoretically the device can contain any amount of fibers. From 1–100,000 fibers can be present. However, a range of 200–25,000 fibers, preferably 3000–15000 fibers, has been found to give the most significant results, especially with inorganic gases.

It is to be understood that although the diffusion device of the present invention is herein described primarily for its application in a gaseous contaminant dosimeter, the invention is also useful in other applications where flow restriction or diffusional transfer are important, such as molecular separation of two species having different diffusivities.

The diffusion device is particularly useful in gaseous contaminant dosimeters because of its ability to integrate, that is, indicate the average concentration of a gaseous contaminant over a given period of time. This is achieved by passively sampling the gaseous contaminant in the ambient air in proportion to its concentration therein by allowing diffusion of the contaminant, according to Fick's Law, into the interior of a receptacle where it is maintained until it is analyzed.

In this regard, a personal dosimeter according to the present invention, in its simplest form, consists essentially of the diffusion device in combination with a receptacle for the gaseous contaminant which can contain a collecting medium therefor. The collecting medium holds the gaseous contaminant or its ions in a form more readily analyzable than the gaseous form. When assembled for use, the diffusion device is imbedded in the receptacle such that one end of the fiber formation is open to the atmosphere and the other end communicates with the interior of the receptacle. The interior of the receptacle is otherwise sealed in an air-tight and liquid-tight manner from the atmosphere although this is not meant to exclude the possibility that the receptacle can have, for example, a removable cap which can be so sealable. The collecting medium can be either next to or apart from the fiber ends that open into the interior of the receptacle.

The material of construction of the receptacle should be impermeable and inert to the gaseous contaminant and the collecting medium. It can be rigid or pliable. Glass, metals, or any of the polymeric materials such as polystyrene, polyethylene, or polypropylene, conventionally used in the construction of laboratory test-tubes, vials, or cuvettes are suitable. The perfluorinated polymers of ethylene and propylene, such as Teflon ®, available from E. I. du Pont de Nemours and Company, are also useful.

The size of the dosimeter is most conveniently "pocket-sized" so that it is readily worn or carried by the person exposed to the contaminant being measured.

As an illustration, such a dosimeter can be constructed from a conventional molded-polystyrene laboratory cuvette of 5 ml volume having a removable cap which is engageable with the cuvette in an airtight and liquid-tight manner. A plug-like diffusion device of the type shown in FIG. 1 is made as described above, using Epi-Rez ® 50821 epoxy as the potting material, to contain 6600 hollow, polypropylene fibers each having 50 micron outside diameter, 30 micron inside diameter. Both this epoxy and polypropylene are gas-impermeable. The fibers in this device are approximately 3.15 mm in length and are potted in parallel fashion in a formation of about 6.35 mm in diameter.

A circular hole corresponding to the diameter of the fiber-formation of the diffusion device is bored into the cap of the cuvette and the fiber-formation is force-fit into the hole and sealed therein around its perimeter with additional potting material. Thus, when the cap is placed on the cuvette, the hollow fibers provide the only communication between the interior of the cuvette and the atmosphere. For purposes of subsequent illustration, the above specifically-described dosimeter will be referred to as the prototype.

Optionally, a porous, hydrophobic film of 15–7500 micron thickness can be placed over the fiber openings on the side of the diffusion device communicating with the interior of the receptacle of the dosimeters of this invention. The film can be made, for example, of polymers or copolymers of tetrafluoroethylene and hexafluoropropylene. It has been found that the presence of such a film does not interfere with the passage of the gaseous contaminant from the interior ends of the fibers to the collecting medium. This is true regardless of the porosity of the film or the size of the pores. The function of the film is to prevent the collecting solution, if that form of collecting medium is used, from flowing into the hollow fibers. This can be accomplished using a film which is 50–80% porous having a pore size of about 0.1–3.0 microns. A suitable substance for this purpose is Gortex ® sold by W. L. Gore and Associates.

Generally, the collecting medium is a material which absorbs, adsorbs, reacts or otherwise combines with the gaseous contaminant being measured. Regardless of the manner in which the collecting medium interacts, as above, with the gaseous contaminant, the quantity or strength of the collecting medium must be sufficient to completely interact with the total quantity of contaminant which it contacts. The collecting medium will often be specific to the particular gaseous contaminant being monitored. Examples, meant to be representative but not limiting, include aqueous solutions of oxidizing agents or triethanol amine to absorb nitrogen dioxide, solutions of potassium or sodium tetrachloromercurate to absorb sulfur dioxide, and solutions of sulfuric or other acids to absorb ammonia. Charcoal or powdered carbon of high surface area and metal powders or films can be used to adsorb many organic gaseous contaminants.

In use, such a dosimeter as previously described is partially or totally filled with a collecting medium, chosen with respect to the particular contaminant being monitored, and can be carried with the exposed person or placed in a position where it will be exposed to an ambient air sample representative of the air to which the subject person is exposed. After exposure for a period of time, the collection medium is analyzed for content of the gaseous contaminant. Values for levels of gaseous contaminant present can be mathematically related to ambient concentration by application of Fick's Law, giving the average level of exposure during the exposure period.

Analysis can be accomplished by withdrawing part or all of the collecting medium and measuring photometrically the spectral characteristics with spectrophotometer, colorimeter, etc., or by measuring the thermal, chemical, or physical properties of the collecting medium. A preferred method, when the collecting medium is an absorbing solution, is to treat the absorbing solution with specified reagents to produce color, the intensity of which is dependent upon the concentration of the gaseous contaminant in solution, and then to determine concentration with a previously calibrated colorimeter or spectrophotometer.

Methods for colorimetric analysis, for example, for sulfur dioxide, nitrogen dioxide, and ammonia, in air, are described in National Institute for Occupational Safety and Health method numbers 160(publication 121, 1975), 108(publication 136, 1974), and 205(publication 121, 1975), respectively. The techniques detailed in these publications are readily adaptable for use in analyzing absorbing solutions from exposed dosimeters of the present invention.

Calculations involving Fick's Law can be obviated by calibrating the dosimeters of this invention to give a direct relationship between colorimetric or spectrophotometric readings and ambient concentration of the gaseous contaminant. As an example of such a calibration procedure, 16 of the previously described prototype cuvette dosimeters were filled with 4 ml of a collecting medium of a 0.1 normal solution of sulfuric acid in deionized, distilled water. Each dosimeter used a porous hydrophobic layer, previously described, of 75 micron thickness having a pore size of approximately 0.2 microns and a porosity of 50–95%. For a period of 8 hours, a group of 4 dosimeters was exposed to air having 14.2 parts ammonia per million parts air (ppm), a second group of 4 exposed to air having 20.0 ppm ammonia, third group of 4 to 52.1 ppm ammonia, fourth group of 4 to 73.9 ppm ammonia. After exposure, to the sulfuric acid solution in each of the 16 dosimeters was added 0.5 ml of Nessler's Reagent ($KI:HgI_2:NaOH$ in weight relationship of 2.2:1:20).

The addition of the Nessler's Reagent caused various intensities of yellow color to appear in the solutions. After allowing 5 minutes for the color to appear fully, each of the sixteen solutions, grouped according to the ammonia concentration to which it was exposed, was withdrawn from its dosimeter and tested for its absorbance at 425 nm in a spectrophotometer using a 1-cm optical cell. The spectrophotometer had been previously set to indicate no absorbance as 0.0 and 100% absorbance as 2.0 on a linear scale. The results are tabulated below:

| Exposure level (ppm $NH_3$/8-hours) | Absorbance at 425 nm (4 dosimeters) |
|---|---|
|  | 0.118 |
|  | 0.150 |
| 14.2 | 0.169 |
|  | 0.191 |
|  | 0.48 |
| 20.0 | 0.57 |
|  | 0.41 |
|  | 0.41 |
|  | 1.12 |
| 52.1 | 1.10 |
|  | 1.21 |
|  | 1.10 |
|  | 1.66 |
| 73.9 | 1.65 |
|  | 1.62 |
|  | 1.84 |

To calibrate the dosimeter to determine a correlation between spectrophotometer readout and 8-hour time-average concentration of contaminant, the best straight line, using a least squares analysis, through these data points is plotted on a linear graph of 8-hour time-average concentration versus absorbance (scale of 0.0–2.0).

A most preferred embodiment of a dosimeter within the present invention is a self-sufficient unit which contains pre-measured amounts of the collecting medium, in an interior receptacle, and the color-forming reagents, separately sealed within the dosimeter but capable of being brought into contact with the collecting medium in the interior receptacle. The dosimeter is adapted to allow analysis of the collecting medium directly, without its being withdrawn from the receptacle.

Such a dosimeter is shown in FIGS. 3 and 4 and is described and can be formed as follows. A base sheet 7 of impermeable polymeric material, which is preferably pliable, is provided with at least one depression 6. Normally, there will be several depressions 6 which can be linearly spaced along a periphery of the sheet 7 as shown. The sheet is preferably transparent and thermoplastic and can be made of polymers of olefin, halogenated polymers, polyester, or ionomer resins. Preferred materials are shown in U.S. Pat. No. 3,264,272 issued Aug. 2, 1966 to R. W. Rees. They are the ionic copolymers of alpha-olefins and alpha, beta-ethylenically unsaturated carboxylic acids of 3–8 carbon atoms having 10–90% of the carboxylic acid groups neutralized with metal ions.

The size of sheet 7 is not critical but is preferably a size easily adaptable for use in a personal dosimeter which is to be worn or readily carried. The depressions 6 can be easily formed by applying pressure to sheet 7 with an appropriate die, heated or otherwise.

Pre-measured amounts of reagents are placed in any convenient manner in the depressions 6. The collecting medium is placed in the central portion of sheet 7. When the collecting medium is a liquid, this can be more easily accomplished by first forming a depression in the central portion of the sheet in a manner similar to the formation of depressions 6. This central depression is normally larger than any of depressions 6.

After the reagent and collecting medium have been placed on sheet 7, a second, top sheet 8 corresponding to sheet 7 in composition and substantially in size is placed over sheet 7. Heat and pressure are then applied to the areas B surrounding the reagent-containing depressions 6 with, for example, a conventional heat-sealing die, thereby forming separate compartments for each reagent. The seals along areas B are purposely made breakable by carefully controlling the heat input or by forming only a narrow seal. Specifically, the formation of the seals can be controlled to provide seals capable of being later ruptured by the application of pressure to the reagents in the compartments. Alternatively, adhesives or other forms of bonding can be used, provided that rupturable bonds are formed in these areas. Heat and pressure are then applied to the three areas A to provide permanent, fluid-tight bonding at the three corresponding edges of sheets 7 and 8.

A gas diffusion device 3 of the ribbon type previously described in connection with FIG. 2 is positioned parallel and proximate to the fourth, unbonded edge of base sheet 7 and parallel and flush with the fourth, unbonded edge of top sheet 8. The hollow fibers of diffusion device 3 are thus oriented horizontally with respect to the plane of sheet 7 and prependicularly with respect to the fourth edges of sheets 7 and 8. The diffusion device 3, thus sandwiched between sheets 7 and 8, is bonded to said sheets by the application of heat and pressure or by use of adhesives which should be impermeable and chemically inert to the collecting medium and reagents.

The bond between the diffusion device 3 and each of said sheets should be liquid-tight and air-tight, thus completing the formation of reaction chamber 5, the reaction chamber being the interior of the sealed receptacle formed between sheets 7 and 8 and containing the collecting medium. The relative positions of the diffusion device 3 and sheets 7 and 8 are such that one end of the hollow fibers, at edge 4 is open to the atmosphere and the other end, at edge 9, communicates with the interior of reaction chamber 5. When the collecting medium is a liquid, a porous, hydrophobic film, as previously described, can be joined to edge 9.

It is also possible to form the preferred dosimeter of FIG. 3 saving the placement of the reagents and collecting medium for last. In such a case, the dosimeter is otherwise formed as described above. The reagents and collecting medium can be placed by piercing top sheet 8 at an appropriate spot with a hypodermic needle and injecting a measured amount of the collecting medium or reagent into the appropriate chamber or compartment. The holes made by the hypodermic needle can then be thermally sealed.

Additionally, the diffusion device used in the preferred dosimeter can be a plug-like device as in FIG. 1 rather than the ribbon-like device of FIG. 2. In such a case, the plug can be sealed into either sheet 7 or sheet 8 so that the relationship of the diffusion device, and the hollow fibers therein, to the reaction chamber is as previously described with respect to the ribbon-like diffusion device.

Except for the inclusion of a diffusion device, the receptacle of the preferred dosimeter is substantially similar to the test pack shown in U.S. Pat. No. 3,476,515 issued Nov. 4, 1969. The disclosure of this patent is incorporated by reference herein.

In use, the preferred dosimeter is exposed to the air containing the gaseous contaminant for a period of time for which the average contaminant concentration is sought. After exposure, the selected reagent compartments, containing the reagents necessary for analysis, are broken, their contents being released into the reaction chamber and mixed with the collecting medium therein. Breaking of the compartment is most easily accomplished by the application of pressure thereto, for example by finger squeezing. The reagents and collecting medium can be thoroughly mixed by application of a light, pulsing force by the fingers on the pliable sheets forming the reaction chamber.

Since the preferred dosimeter is pliable and transparent, the contents of the reaction chamber can be analyzed directly without withdrawing a sample from the dosimeter. If the analysis is to be made photometrically, then the dosimeter can be clamped in a position where electromagnetic radiation can be directed through the contents of the reaction chamber with the unabsorbed (i.e., transmitted) radiation being directed to an appropriate detector. The preferred method is to use reagents which change the color of the collecting medium, depending on the amount of gaseous contaminant collected, and then analyzing with radiation in the range of visible light using a colorimeter or spectrophotometer.

To facilitate such analysis, the dosimeter can optionally include means for clamping the dosimeter in a suitable position such that a constant-depth optical cell is formed. An example of such means is a ring-shaped member having radially directed through-and-through channels which is attached within the reaction chamber to the interior face of either of sheets 7 or 8. The thickness of the ring determines the optical depth and the channels ensure that a sample of the contents of the reaction chamber will fill the optical cell formed by the central space of the ring.

As an example of the integrating capabilities of the gas diffusion device of this invention, 8 cuvette dosimeters, identical to the prototype cuvette dosimeter except that the diffusion device contained 10000 hollow fibers, were each filled with 4 ml of a 0.1 normal solution of sulfuric acid in deionized, distilled water. Each dosimeter was given an exposure of approximately 200 ppm-hours of ammonia: Four of the dosimeters (Group 1) were exposed to air having approximately 33.5 ppm ammonia for a period of 6 hours; the remaining 4 dosimeters (Group 2) were exposed to air having approximately 87.3 ppm ammonia for a period of 2.5 hours.

After the exposures, each dosimeter was analyzed using Nessler's Reagent and a spectrophotometer as previously described. For Group 1, the average absorbance of the 4 dosimeters was 0.72; for Group 2, the average absorbance of the 4 dosimeters was 0.75, indicating substantially equivalent collection of gaseous contaminant for exposures of different intensities but similar integrated totals.

I claim:
1. A gas diffusion device to restrict the flow of a gaseous contaminant which comprises:
   a plurality of parallel, potted, hollow fibers, said fibers being substantially non-hygroscopic, having an inside diameter of 15–500 microns a length of from 2.0 to 8.0 mm and being made of polypropylene, polyethylene, polyethylene terephthalate, or polymers or copolymers of tetrafluoroethylene and hexafluoropropylene; and
   potting material which fills all the longitudinal spaces between said fibers,
wherein at least one of said fibers and said potting material is impermeable to said gaseous contaminant.

2. The diffusion device of claim 1 having at least 200 fibers.

3. A gas diffusion device to restrict the flow of a gaseous contaminant which comprises:
   200–25,000 parallel, potted hollow fibers having an inside diameter of 15–45 microns and a length of 2.0–8.0 mm, said fibers being made of polypropylene, polyethylene, polyethylene terephthalate, or polymers or copolymers of tetrafluoroethylene and hexafluoropropylene; and potting material which fills all the longitudinal spaces between said fibers, said potting material being selected from the group consisting of paraffin waxes, epoxy-based polymerics, and ionomer resins wherein at least one of said fibers and said potting material is impermeable to the gaseous contaminant.

4. The gas diffusion device of claim 3 in the form of a plug.

5. The gas diffusion device of claim 3 in the form of a ribbon.

6. A dosimeter for the detection of a gaseous contaminant comprising:

a closed receptacle; and a gas diffusion device, forming a part of a boundary of said receptacle, which comprises a plurality of parallel, potted, hollow fibers, said fibers being substantially nonhygroscopic and inert to said gaseous contaminant and having an inside diameter of 15–1000 microns, and potting material which fills all the longitudinal spaces between said fibers wherein at least one of said fibers and said potting material is impermeable to said gaseous contaminant, and wherein said hollow fibers provide the only communication between the atmosphere and the interior of said receptacle.

7. The dosimeter of claim 6 wherein said fibers are polypropylene, polyethylene, polyethylene terephthalate, or polymers or copolymers of tetrafluoroethylene and hexafluoropropylene.

8. The dosimeter of claim 7 wherein said fibers have an inside diameter of 15–500 microns and wherein said receptacle contains a collecting medium capable of interacting with the gaseous contaminant.

9. The dosimeter of claim 7 or claim 8 further comprising a porous, hydrophobic inert film in contact with the ends of said fibers which are open to the interior of said receptacle.

10. A dosimeter for the detection of a gaseous contaminant comprising:

a pouch-like receptacle of polymeric material having at least one compartment, said compartment occupying less than the total volume of said receptacle, leaving a reaction chamber, said compartment being adapted to contain a predetermined quantity of a testing reagent and said compartment being further adapted to release said reagent into said reaction chamber independently of any other reagents present in any other compartments, said reaction chamber being adapted to contain a collecting medium for said gaseous contaminant; and a gas diffusion device, sealed into a boundary of said receptacle, which comprises a plurality of parallel, potted, hollow fibers, said hollow fibers being substantially non-hygroscopic and inert to said gaseous contaminant and having an inside diameter of 15–1000 microns, and potting material which fills all the longitudinal spaces between said hollow fibers wherein at least one of said hollow fibers and said potting material is impermeable to said gaseous contaminant, and wherein said hollow fibers provide the only communication between the atmosphere and the interior of said reaction chamber.

11. The dosimeter of claim 10 having at least 200 fibers wherein said fibers are polypropylene, polyethylene, polyethylene terephthalate, or polymers or copolymers of tetrafluoroethylene and hexafluoropropylene and said potting material is a paraffin wax, an epoxy-based polymeric, or an ionomer resin.

12. The dosimeter of claim 11 further comprising a porous, hydrophobic inert film in contact with the ends of said fibers which are open to said reaction chamber.

13. A dosimeter for the detection of a gaseous contaminant comprising:

a pouch-like receptacle of pliable polymeric material having at least one compartment, said compartment occupying less than the total volume of said receptacle, leaving a reaction chamber, said compartment being adapted to contain a predetermined quantity of a testing reagent and said compartment being further adapted to release said reagent into said reaction chamber independently of any other reagents present in any other compartments, said reaction chamber being adapted to contain a collecting medium for said gaseous contaminant;

a gas diffusion device, sealed into a boundary of said receptacle, which comprises 200–25,000 parallel, potted, hollow fibers, said fibers being made of polypropylene and having an inside diameter of 15–45 microns and being 2.0–8.0 mm in length, and potting material which fills all the longitudinal spaces between said hollow fibers wherein said potting material is a paraffin wax, an epoxy-based polymeric, or an ionomer resin, and wherein said hollow fibers provide the only communication between the atmosphere and the interior of said reaction chamber; and a porous, hydrophobic, inert film in contact with the ends of said fibers which are open to the interior of said reaction chamber.

14. The dosimeter of claim 13 further comprising means within said reaction chamber to facilitate photometric analysis by providing an optical cell.

15. The dosimeter of claim 13 or claim 14 wherein said gas diffusion device is in the form of a ribbon.

16. The dosimeter of claim 13 containing a collecting medium for sulfur dioxide, nitrogen dioxide, or ammonia.

17. The dosimeter of claim 16 further containing at least one testing reagent.

18. The dosimeter of claim 17 wherein the collecting medium is a solution of sodium tetrachloromercurate or potassium tetrachloromercurate in water and the testing reagent is for determining the presence of sulfur dioxide.

19. The dosimeter of claim 17 wherein the collecting medium is a solution of triethanol amine in water and the testing reagent is for determining the presence of nitrogen dioxide.

20. The dosimeter of claim 17 wherein the collecting medium is a solution of sulfuric acid in water and the testing reagent is for determining the presence of ammonia.

* * * * *